United States Patent [19]

Sheingorn

[11] 4,392,725
[45] Jul. 12, 1983

[54] DEVICE FOR BLIND SPOT DELINEATION

[76] Inventor: Larry A. Sheingorn, 3139 Tennyson St., NW., Washington, D.C. 20015

[21] Appl. No.: 124,101

[22] Filed: Feb. 25, 1980

Related U.S. Application Data

[63] Continuation-in-part of Ser. No. 966,793, Dec. 5, 1978, abandoned.

[51] Int. Cl.³ .............................................. A61B 3/02
[52] U.S. Cl. ................................................... 351/224
[58] Field of Search ............................ 351/23, 24, 30

[56] References Cited

U.S. PATENT DOCUMENTS

| | | | |
|---|---|---|---|
| 3,288,546 | 11/1966 | Gans | 351/24 |
| 3,421,498 | 1/1969 | Gans | 351/24 X |
| 3,705,003 | 12/1972 | Lynn et al. | 351/39 |
| 3,718,386 | 2/1973 | Lynn et al. | 351/39 |
| 3,883,234 | 5/1975 | Lynn et al. | 351/23 |
| 3,883,235 | 5/1975 | Lynn et al. | 351/23 X |
| 3,982,828 | 9/1976 | Woolf | 351/23 |
| 4,059,348 | 11/1977 | Jernigan | 351/30 |

OTHER PUBLICATIONS

D. Regan et al., "Visual Field Analyzer" Medical & Biological Engineering, vol. 14, No. 1, p. 8-14, Jan. 1976.

*Primary Examiner*—John K. Corbin
*Assistant Examiner*—Rodney B. Bovernick
*Attorney, Agent, or Firm*—Charles R. Wolfe, Jr.

[57] ABSTRACT

A self-contained, solid state device, with no moving parts, that determines visual field defects is disclosed. The device employs a tangent screen containing LEDs which are illuminated in sequence to test the visual field of the patient. The device utilizes a memory unit for recording and displaying the test results.

4 Claims, 21 Drawing Figures

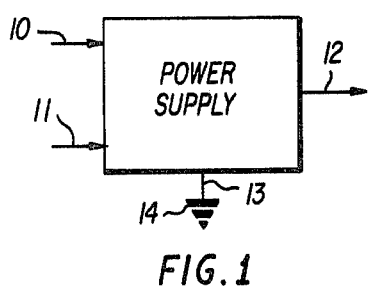
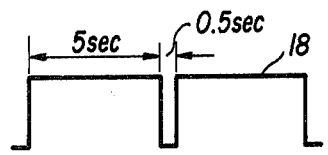
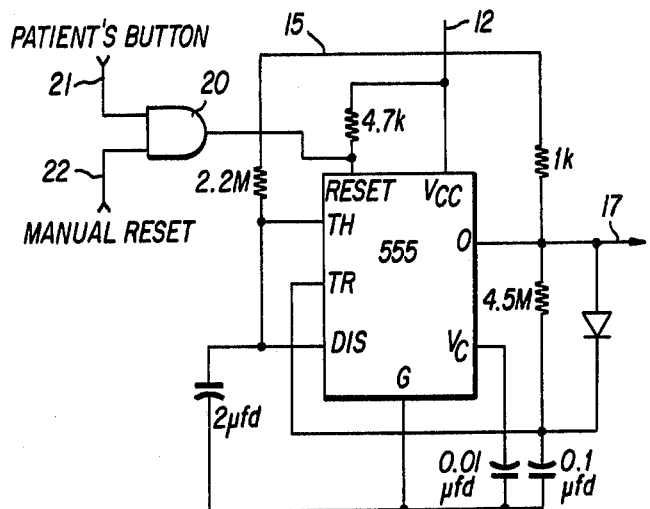
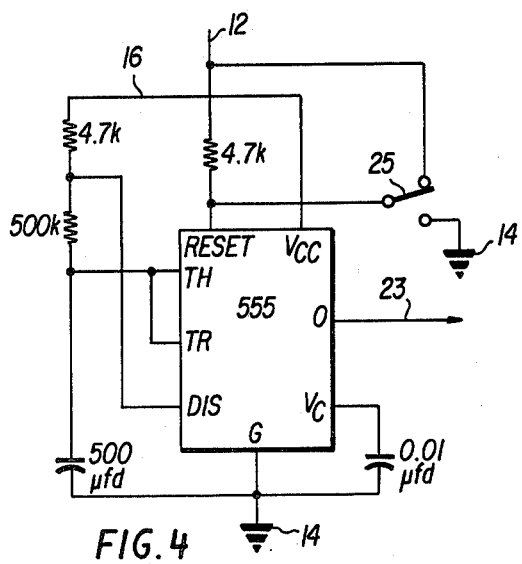
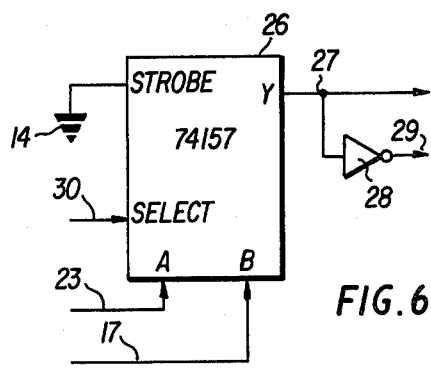
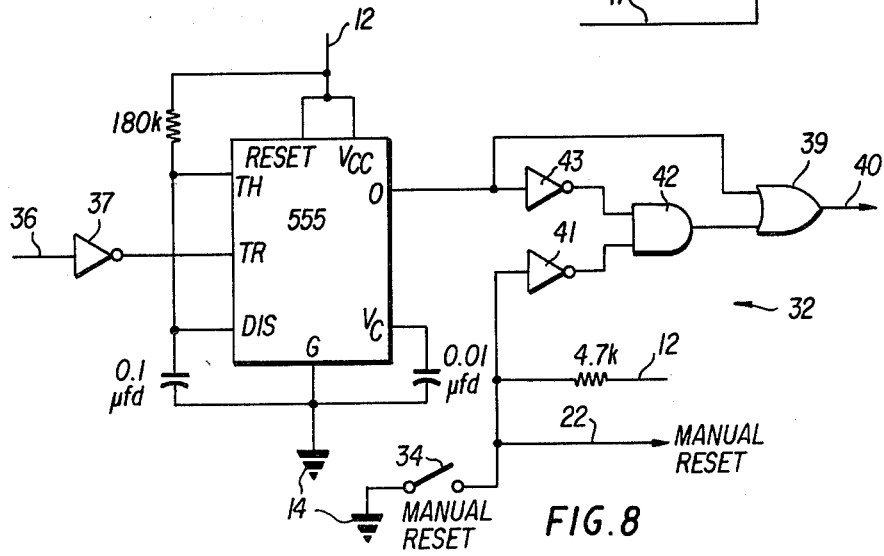

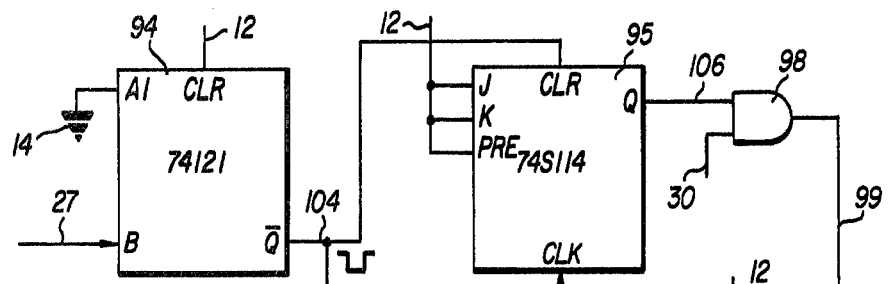
FIG. 18
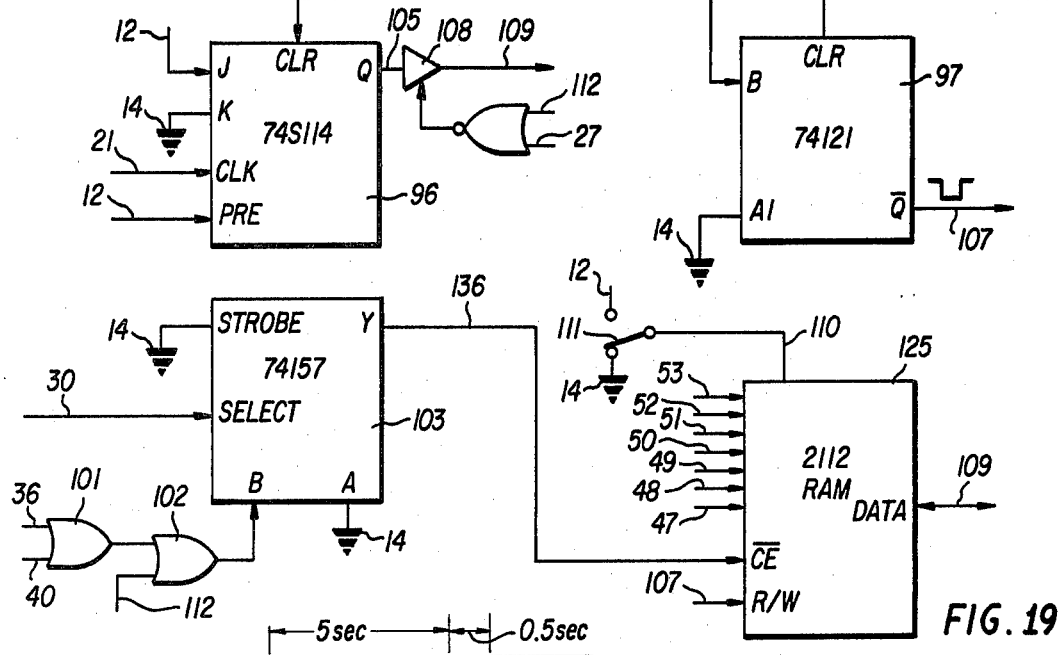
FIG. 19
FIG. 20
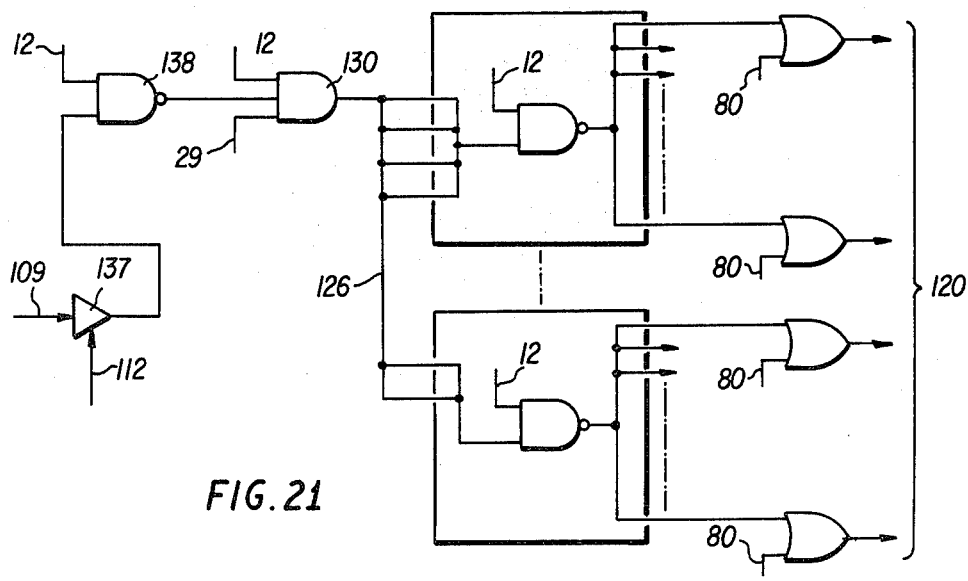
FIG. 21

DEVICE FOR BLIND SPOT DELINEATION

CROSS REFERENCE TO RELATED APPLICATION

This application is a continuation-in-part of application Ser. No. 966,793, filed Dec. 5, 1978 now abandoned.

BACKGROUND OF THE INVENTION

1. Field of the Invention

The present invention is directed to a device for determining visual field defects in humans.

2. Description of the Prior Art

Blind spot delineation is of unquestioned opthamological value in the diagnosis and management of various disease states. It is a frequent procedure in routine eye examinations as well. Unfortunately, it is a tedious task, which, up to now, has either involved numerous human examiner errors, or complex machinery with many mechanical parts and/or highly sophisticated, expensive data processing equipment. In many existing methods of examination, a hard copy of the test results is either printed in real time on special paper, before it can be determined if the results are worth saving, or is manually drawn by the human examiner.

SUMMARY OF THE INVENTION

In contrast to the aforementioned devices presently available for blind spot delineation, the apparatus of the present invention is an inexpensive, self-contained, portable, easily modified and expanded device that delineates blind spots via a type of tangent screen static perimetry. Furthermore, it automatically stores the patient's responses in a solid state memory system that can store as many complete eye examinations as desired, which enables it to repeat exams for subject reliability determinations, conduct both right and left eye examinations, etc. Upon command, the device will display the "blind spots" of any particular test by illuminating all lights that the patient did not see in that test. Different tests can easily be compared, and, if a hard copy is desired, a picture may be taken of the display by an instantly developing camera. Thus, if the examiner believes no new information has been obtained, he does nothing. On subsequent tests, new data will be electronically written over the old.

BRIEF DESCRIPTION OF THE FIGURES OF DRAWING

FIG. 1 is a schematic view of the power supply for the device of the invention.

FIG. 2 is a schematic view of one of two circuits which make up the first system clock in the device of the invention.

FIG. 3 represents the signal produced by the circuit of FIG. 2.

FIG. 4 is a schematic view of the second of two circuits which make up the first system clock in the device of the invention.

FIG. 5 represents the signal produced by the circuit of FIG. 4.

FIG. 6 is a schematic view of the circuitry which selects the signal from the first system clock.

FIG. 8 is a schematic view of the second system clock of the device of the invention.

FIG. 18 is a schematic view of the data processing circuitry of the device of the invention.

FIG. 19 is a schematic view of the data read/write circuitry of the device of the invention.

Figure 7:
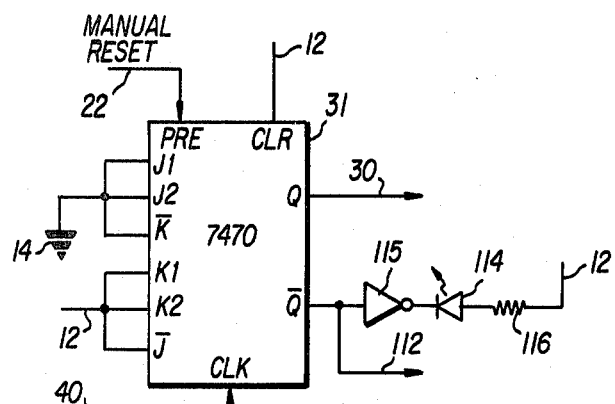
FIG. 7 is a schematic view of the stop write circuitry of the device of the invention.

FIG. 20 graphically depicts the operation of the circuits shown in FIGS. 18 and 19.

FIG. 21 is a schematic view of the read drive circuitry of the device of the invention.

The non-reference identifying numbers in the figures of drawing identify specific integrated circuits in accordance with accepted manufacturer's nomenclature.

DETAILED DESCRIPTION OF THE INVENTION

The foregoing features of the present invention are provided by a device which comprises two main parts. First, there is a tangent screen similar to ones found in almost every opthamologist's office. It is a board covered with a dark material, such as black felt, generally just slightly over a square meter in area. The device of the present invention modifies this board by placing as many small light emitting diodes (LEDs) as desired at appropriate positions in this board so that individual light sources shine through the surface. In this manner, the same board can be used conventionally by simply covering the LED's surfaces with another piece of dark material. This material is removed to expose the LEDs when the device is operated.

The second major part of the device of the present invention is a control box. It has three cables emanating from it. One plugs into a standard wall socket, another connects with the modified tangent screen, and the third connects to a small push button that the patient presses during the examination when a light becomes visible to him. The control box contains all the electronics for determining which one of all the possible lights is lit, for evaluating whether the patient has responded to that light, for storing that information, for moving on to the next light when the patient has responded or after a predetermined period in which the patient has failed to respond, for signaling when the particular test in progress is completed, and for displaying the appropriate test data on the tangent screen as called for by the examiner.

According to a preferred embodiment of the invention, the tangent screen contains 127 LEDs which are, as far as the patient is concerned, randomly presented to him. The test may be repeated with the lights at different levels of brightness, often a useful comparison, by merely adjusting a dial (FIG. 16) which controls the intensity of the LEDs and repeating the test. The device of the invention stores two tests in its one-chip memory, but for nominal expense, this storage capacity can be easily expanded. As many LEDs may be added as desired to further delineate borders of the blind spots, using additional address counters, one of n decoders, and memory.

Reference to the figures of drawing illustrates a particular embodiment of the present invention. The control box is seen to be composed of several sections. As shown in FIG. 1, there is a conventional power supply that allows the device to be plugged into any wall socket via lines 10 and 11. Typically, this power supply generates 5 volts at 6 amperes, after regulation, thus supplying all needed power for the TTL logic memory devices and lamps through line 12 and line 13 which is connected to ground 14.

The system is orderly run by three system clock circuits. The first system clock consists of two circuits 15 and 16, shown schematically in FIGS. 2 and 4, respectively. Circuit 15 is an astable multivibrator circuit which generates a signal through line 17. This signal is labeled 18 in FIG. 3. The astable multivibrator of circuit 15 is controlled by line 19 from AND gate 20 having input lines 21 and 22 which are connected to the patient's button circuit and the second system clock as described in detail hereinafter.

Circuit 16 is another astable multivibrator circuit which generates a signal through line 23. This signal is labeled 24 in FIG. 5. Circuit 16 additionally contains a switch 25 which either holds the signal 24 in a logical low or allows it to run normally, typically at 3 kHz.

As shown in FIG. 6, the first system clock's output, which is either signal 18 or signal 24, is directed through lines 17 and 23 to circuit 26 which selects either one and directs it through line 27. Circuit 26 comprises a 2-line-to-1-line data selector/multiplexer. Circuit 26 also contains an inverter 28 which inverts signal 27 and directs the inverted signal through line 29. The selection of signals 18 or 24 by circuit 26 is controlled by line 30 from stop write circuit 31, depicted in FIG. 7, as described in detail hereinafter.

Figure 9:
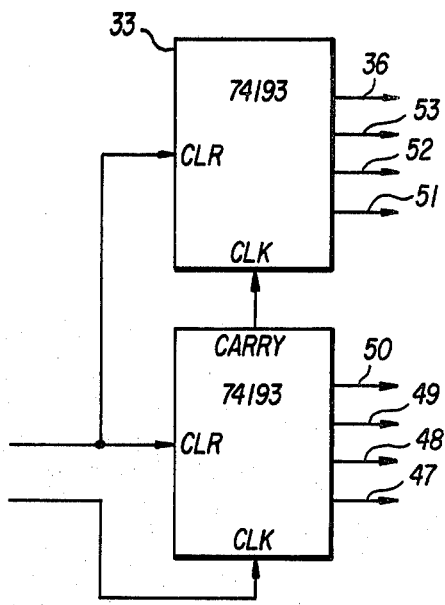
FIG. 9 is a schematic view of the address generators of the device of the invention.

The second system clock 32, shown in FIG. 8, includes a pulse generator circuit 35, and is provided to reset the address counters 33 shown in FIG. 9, when all the lights have been tested and to switch the device from its write mode to its waiting to read or auto read mode, depending upon the setting of switch 25 in the first system clock. When beginning a test, a reset button 34 is pressed. This puts the device in the write mode and starts it at the first lamp 0.5 seconds after the button is released. While the reset button 34 is held down, a lamp on the control box lights with essentially the same intensity as the other stimulating LEDs.

Figure 10:
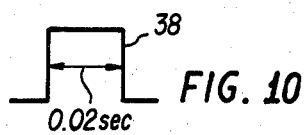
FIG. 10 represents the signal produced by the second system clock circuit of FIG. 8.

The pulse generator 35 is triggered by a signal from the address counters 33 directed through line 36 and inverted by gate 37 to produce the signal labeled 38 in FIG. 10. Logic gates 39, 41, 42 and 43 allow pulse generator 35 to reset the address counters and stop write circuitry of FIG. 7 in the read mode. These gates also permit the reset button 34 to simultaneously reset the address counters and place the stop write circuitry 31 in the write mode when the reset button is depressed.

Figure 11:
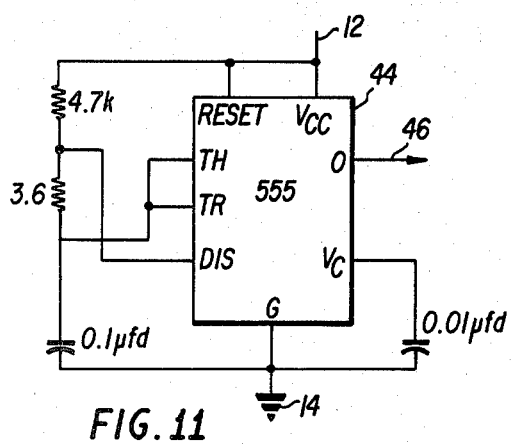
FIG. 11 is a schematic view of the third system clock of the device of the invention.
Figure 12:
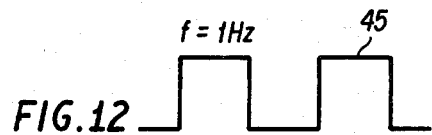
FIG. 12 represents the signal produced by the third system clock of FIG. 11.

The third system clock 44, shown in FIG. 11, is an astable multivibrator which generates a 1.0 Hz signal labeled 45 in FIG. 12 which is directed through line 46. This clock flashes the presented stimuli on and off rapidly during the write mode. The clock is not used during the read operation.

Figure 13:
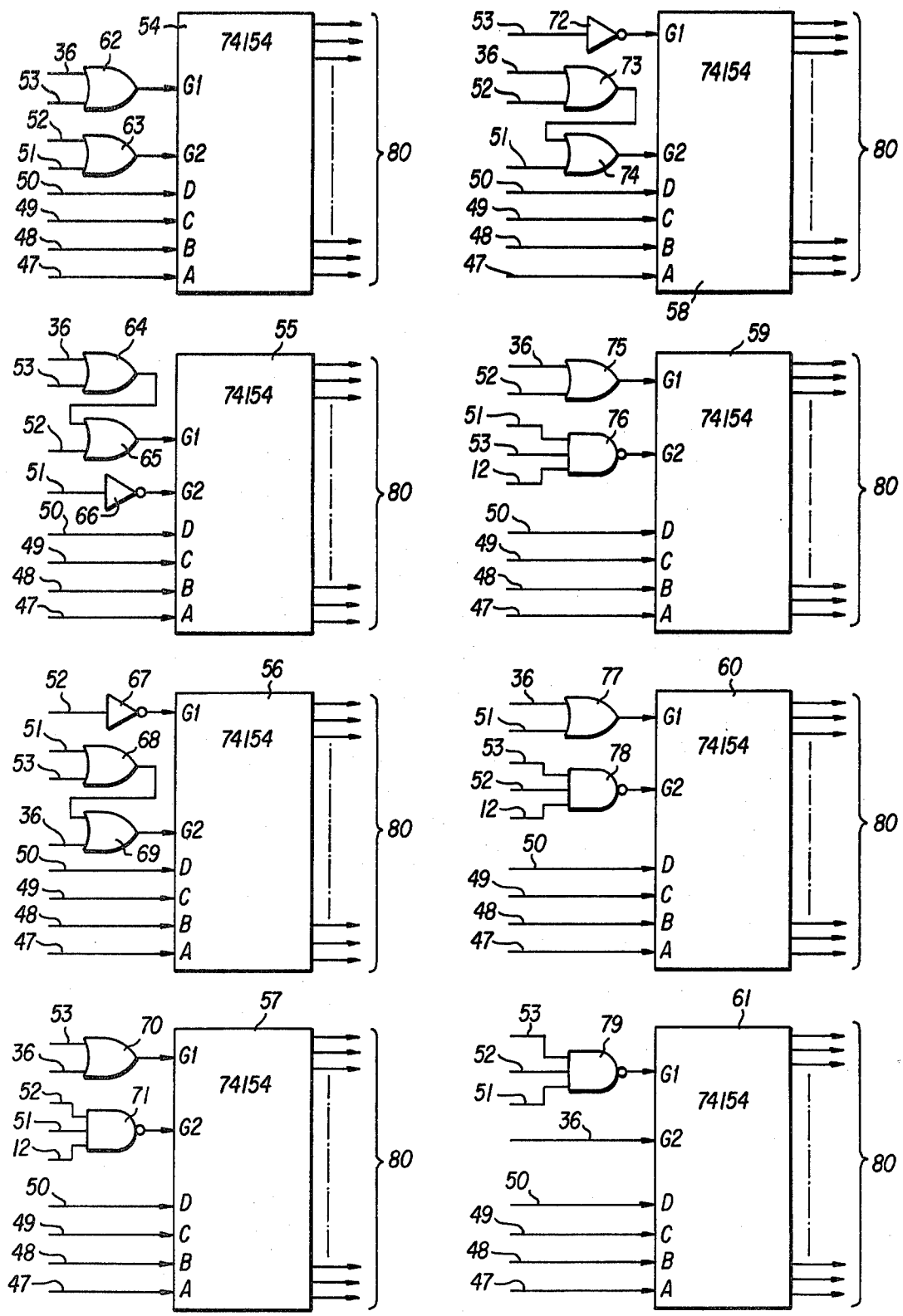
FIG. 13 is a schematic view of the circuitry which produces the data to illuminate one of 128 lamps in the device of the invention.

As shown in FIG. 9, there are two address generators which are simply synchronous four bit counters advanced by the positive going portion of the signal transmitted through line 27 from the selected output, i.e, either signal 18 or signal 24, of the first system clock. The eight bit address generated by the address counters is supplied to a "1 of 128" select logic, FIG. 13, through lines 47–53 and 36. The signal in line 36 is also directed to the second system clock 32. When this signal goes high, that is, when the device attempts to count from 127 to 128, the second system clock pulses through line 40 which resets the counters to zero.

Figure 14:
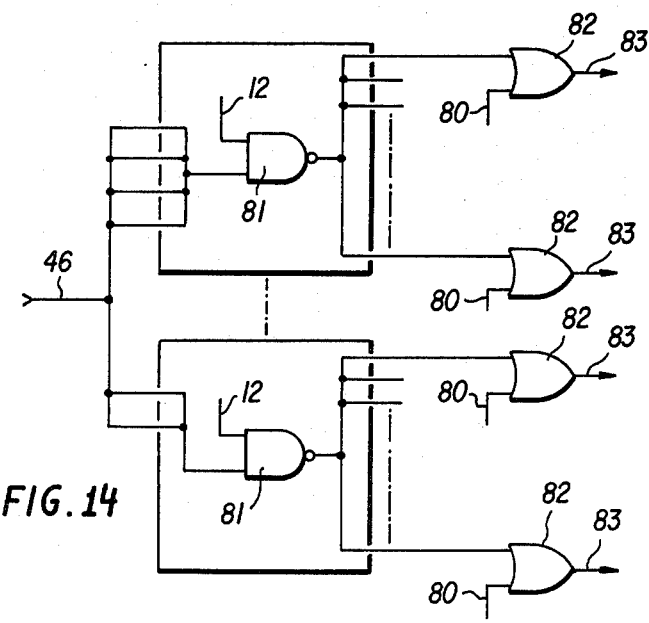
FIG. 14 is a schematic view of the write drive circuitry of the device of the invention.

Referring again to FIG. 13, the device of the invention uses eight "one of sixteen" data multiplexer chips, 54–61 with simple chip enable logic, gates 62–79. Thus, the data to illuminate one of the 128 lamps is generated. This data is supplied to the write drive circuitry, shown in FIG. 14, through one of 128 lines 80, where it is ANDed with the signal from the third system clock from line 46. In this manner, signal 45 from the third system clock is directed through one of the 128 lines 83, exiting the write drive circuitry.

Figure 15:
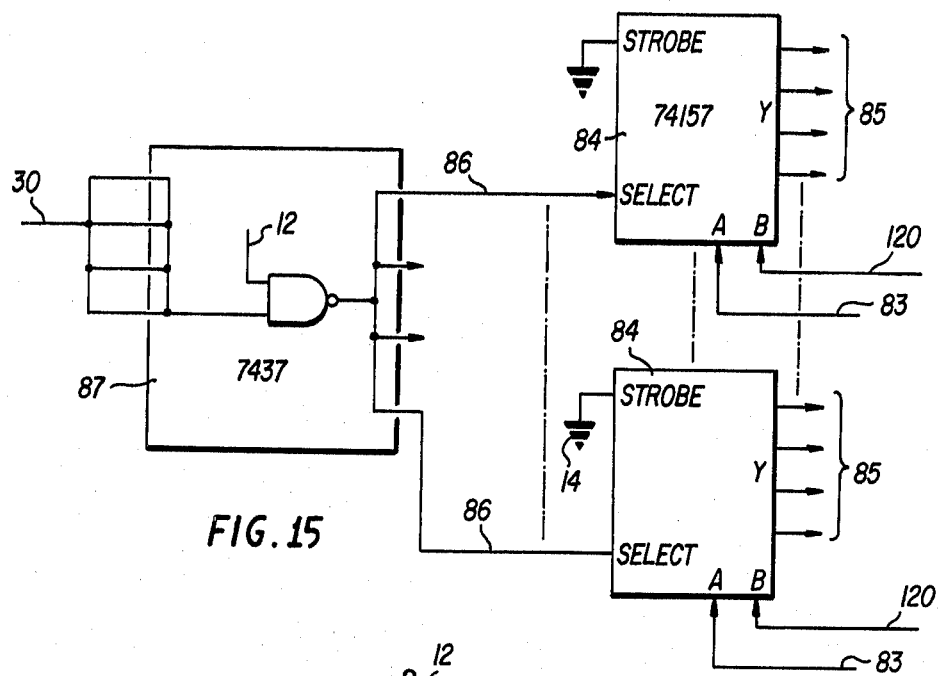
FIG. 15 is a schematic view of the data selection circuitry of the device of the invention.

As shown in FIG. 15, the signals on lines 83 are connected to data selectors 84. There are thirty-two data selectors, each connected to four of the lines 83. The output from the data selectors is connected through lines 85 to the 128 LEDs shown in FIG. 16. The stop write signal generated by the circuitry of FIG. 7 is transported by line 30 through buffers 87 to produce signals through lines 86 which control the data selectors 84. Thus, when the device is in the write mode, i.e., when it is testing the patient, one and only one of the LEDs blinks in response to one of the 128 signals transmitted through lines 85.

Figure 16:
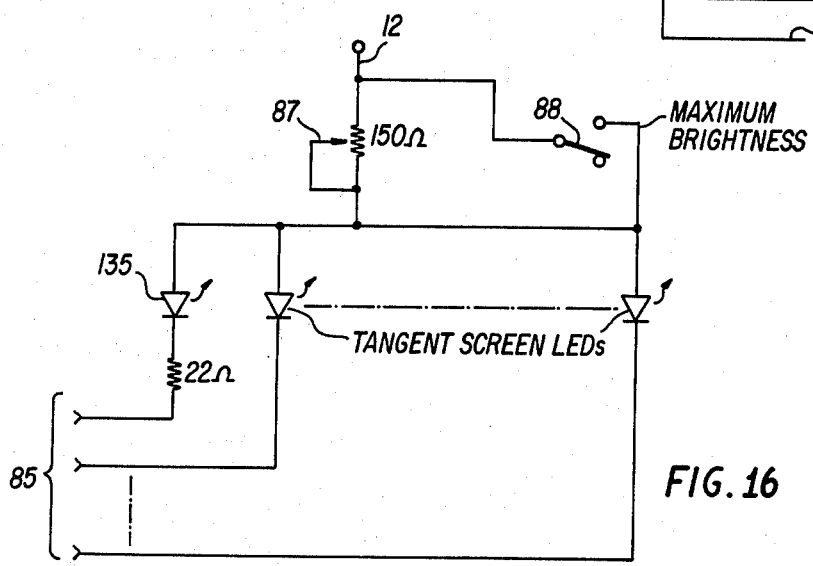
FIG. 16 is a schematic view of the lighting circuitry in the device of the invention.

Referring to FIG. 16, all of the anodes of the LEDs are connected to the output of the power supply through line 12 and through rheostat 87. The setting of this rheostat varies the brightness of the LED. Alternately, the anodes may be directly connected to line 12 of the power supply by closing switch 88. LED 135 is illuminated when the reset button is depressed before the test begins to show the examiner the approximate brightness of the stimuli.

Figure 17:
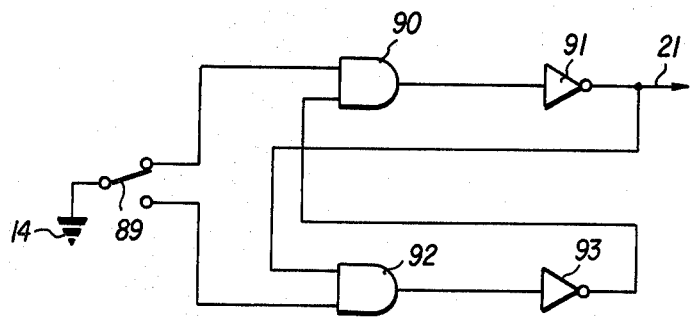
FIG. 17 is a schematic view of the patient's button which transmits a signal when depressed.

In conducting a test using the device of the invention, the patient holds a button 89, pictured in FIG. 17, which in conjunction with logic gates 90–93 determines the signal transmitted on line 21. When the button is depressed, the signal on line 21 becomes a logical low. This signal is transmitted into data processing circuitry shown in FIG. 18. The data processing circuitry is comprised of a pulse generator 94, triggered by the rising edge of signal 18 transmitted through line 27, a bistable multivibrator 95, triggered by the falling edge of signal 18, a second bistable multivibrator 96, triggered by the signal on line 21, and a second pulse generator 97 which is triggered by the output of multivibrator 95 transmitted through AND gate 98, arriving through 99. Signal 18 is present on line 27 only when the device is in the write mode as a result of the action of circuit 26 (FIG. 6) as described above. Logic gates 108, 98 and 100 work in conjunction with gates 101 and 102 and data selector 103, depicted in FIG. 19, to insure that data obtained during the test is not replaced by additional, spurious data.

During a test, when signal 18 on line 27 goes high, it increments the address counters of circuit 33 (FIG. 9) as previously described and causes pulse generator 94 to output a short negative pulse via line 104. This pulse sets the output lines 105 and 106 of bistable multivibrators 95 and 96 low.

If during the high portion of signal 18, the patient depresses the button 89, the signal on line 21 goes low as previously explained in reference to FIG. 17 and sets the signal on line 105 from bistable multivibrator 96 in FIG. 18 high. Obviously, if the patient fails to respond to a light by depressing the button, this signal remains low.

On the falling edge of signal 18, the signal on line 106 goes high and if the device is in the write mode this signal appears on line 99 through gate 98. The transition of the signal on line 99 from low to high causes pulse generator 97 to produce a brief negative pulse on line 107.

When the device is in the write mode, the logical state of line 105 is transferred to line 109 by action of gates 108 and 100.

Referring to FIG. 19, the data on line 109 is stored in a random access memory integrated circuit 125 at the location specified by the address on lines 47–53 and 110.

The logical state of line 110 can be made low or high depending on the setting of switch 111 to either ground 14 or output of the power supply 12, respectively. The data on line 109 can be written into memory only when there is a brief negative pulse on line 107 and the signal on line 136 is low. Line 136 is low only when the device is in the write mode as a result of the action of gates 101 and 102 and data selector 103.

The operation of the circuits schematically depicted in FIGS. 18 and 19 is graphically shown in FIG. 20.

When the test is complete, the second system clock shown in FIG. 8 produces a pulse 38 (FIG. 10) through line 40 in FIG. 7 which causes the signal on line 30 to go low and the signal on line 112 to go high. Besides illuminating LED 114 (which is not one of the 128 test LEDs) via gate 115 and resistor 116, the signals on lines 30 and 112 prevent further writing into memory as explained in connection with FIGS. 18 and 19, supra, and placed the device in its read mode.

With the device in the read mode, the signal on line 30 is low in circuit 26 (FIG. 6). This causes signal 24 (FIG. 5) to appear on line 27. This, in turn, causes rapid incrementation of the address counters (FIG. 9) if switch 25 (FIG. 4) is in the appropriate position, labeled auto read. Otherwise, the address counters remain at zero.

Referring again to FIG. 19, when in the auto read position, lines 47–53 rapidly repeatedly count in binary from 0 to 127 and are reset to zero by signal 38 through line 40 when the signal on line 36 goes high. During the read operation, the data entered through line 109 in the memory 125 sequentially appears on line 109 according to the address specified by the logical states of lines 47–53 and 110. Circuit 126 depicted in FIG. 21 essentially ANDs the data on line 109, which passes through gates 137 and 138, with the signals from lines 80. Gate 130 insures that the effective AND operation does not occur until the data being read from line 109 is accurate. The resulting output is routed to the circuitry of FIG. 15 through line 120 and appears on lines 85 which causes only those LEDs that the patient failed to respond to during the test to be rapidly illuminated so that they appear to be constantly on. If desired, a photograph of the pattern of illuminated LEDs can be taken to provide a permanent record of the patient's blindspots.

Those skilled in the art will readily appreciate the versitility of the device of the present invention. Since only one LED is ever on at a time, varying the brightness of the test objects can be accomplished by varying the value of one resistor. A Cds cell could be configured to help keep the relative stimuli illumination constant even if the room light varies slightly. Since line 36 is essentially an unused address line (i.e., it is always low), holding the memory's line 36 high or low doubles the amount of complete tests which can be stored in the device. Additional memory chips may be added quite easily—switches simply connect all chip enable lines to disable (line 12 in the figures of drawing), until one particular chip is desired to be used—its chip enable line is then connected to the internal chip enable signal on line 136. A multi-position, single pole switch could drive chip select logic which would make memory chip selection very easy for the operator. The time provided for the patient to respond can be shortened or lengthened by varying one component in the circuitry of FIG. 2.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A self-contained, solid state device, with no moving parts, that determines visual field defects, comprising:
   (a) a surface with lamps mounted therein connected to circuitry which automatically turns on the lamps during testing,
   (b) a spring return push button switch that the patient depresses upon observing a lighted lamp on said surface connected to circuitry which determines when the patient responds to or does not respond to a lighted lamp and stores the information in memory,
   (c) circuitry which reads and processes the stored information connected to circuitry which routes the output when the memory is read to lamps corresponding to the lamps which were presented to the patient, and not responded to by the patient,
   (d) circuitry which determines when the test is complete and
   (e) a power supply which supplies power to drive the circuitry of the device.

2. The device of claim 1, further comprising circuitry for resetting the device after the test is complete.

3. The device of claim 1, further comprising circuitry for signalling the operator when the test is completed.

4. The device of claim 1, further comprising circuitry for adjusting the intensity of the lamps.

* * * * *